(12) United States Patent
Takahashi et al.

(10) Patent No.: US 6,452,021 B1
(45) Date of Patent: Sep. 17, 2002

(54) PROCESS FOR PRODUCING PYROMELLITIC ANHYDRIDE

(75) Inventors: Tsukasa Takahashi, Himeji; Yasuhisa Emoto, Hyogo; Etsushige Matsunami, Himeji, all of (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/963,402

(22) Filed: Sep. 27, 2001

(30) Foreign Application Priority Data

Sep. 28, 2000 (JP) ........................................ 2000-297040
Sep. 28, 2000 (JP) ........................................ 2000-297101

(51) Int. Cl.$^7$ ............................................ C07D 307/77
(52) U.S. Cl. ........................ 549/239; 502/242; 502/247; 502/248
(58) Field of Search ......................................... 549/239

(56) References Cited

U.S. PATENT DOCUMENTS 5,387,699 A    2/1995    Wagner et al. .............. 549/239

FOREIGN PATENT DOCUMENTS

JP    7-2864    1/1995

*Primary Examiner*—Bernard Dentz
(74) *Attorney, Agent, or Firm*—Sughrue Mion, PLLC

(57) ABSTRACT

The present invention has for its object to provide a production method of pyromellitic anhydride of high purity in good yield at low cost by catalytic gas-phase oxidation of a 2,4,5-trialkylbenzaldehyde with the aid of a suitable catalyst system.

The present invention relates to a production method of pyromellitic anhydride comprising a step for catalytic gas-phase oxidation of a 2,4,5-trialkylbenzaldehyde with a molecular oxygen-containing gas in which said step for catalytic gas-phase oxidation is carried out in the presence of a catalyst such that a specific surface area of the catalytic active component thereof is not greater than 50 m$^2$/g or in the presence of a catalyst containing vanadium as well as molybdenum and/or tungsten as a catalytic active component.

8 Claims, No Drawings

PROCESS FOR PRODUCING PYROMELLITIC ANHYDRIDE

FIELD OF THE INVENTION

The present invention relates to a catalyst for use in the production of pyromellitic anhydride and a production method of pyromellitic anhydride. More particularly, the invention relates to a catalyst system suitable for the production method of pyromellitic anhydride by the catalytic gas-phase oxidation of a 2,4,5-trialkylbenzaldehyde and a production method of pyromellitic anhydride with the aid of said catalyst system.

BACKGROUND OF THE INVENTION

Pyromellitic anhydride is in broad use as a starting material of polyimide resin, a plasticizer, and apolyester resin modifying agent, among other uses, and its importance as an industrial material has been increasing steadily in recent years.

The production method of pyromellitic anhydride can be roughly classified into the liquid-phase oxidation method and the gas-phase oxidation method. As regards the liquid-phase oxidation method, the process for nitric acid oxidation of 1,2,4,5-tetramethylbenzene (hereinafter referred to sometimes as "durene") and the process for liquid-phase air oxidation of 2,4,5-trimethylbenzaldehyde are known. But these processes do not give pyromellitic anhydride directly and require conversion of the produced pyromellitic acid to the anhydride. This conversion to the anhydride form is a step entailing a large energy consumption. Moreover, these liquid-phase oxidation processes generate large quantities of waste liquor and cause a substantial corrosion of the equipment so that they have much to be improved not only in economic terms but also in environmental terms.

On the other hand, the gas-phase oxidation method is superior in that it can give pyromellitic anhydride directly, does not require the costly step of conversion to the anhydride, nor does it generate an appreciable amount of waste liquor. However, compared with the liquid-phase oxidation method, the gas-phase method has a drawback of low selectivity and a large number of reports have been made mainly concerning improvement of the catalyst system.

The commonest production method of pyromellitic anhydride by catalytic gas-phase oxidation is the method using durene as a starting material but other examples are also reported using pentaalkylbenzene, hexaalkylbenzene (Japanese Kokai Publication Sho-55-122787), pentaalkylphenol, tetraalkylphenol (Japanese Kokai Publication Sho-55-154966), tetraethylbenzene (Japanese Kokai Publication Hei-3-284646, Japanese Kokai Publication Hei-3-109387, Japanese Kokai Publication Hei-3-284645), anthracene (Japanese Kokai Publication Sho-56-8388), 1-ethyl-2,4,5-triisopropylbenzene (Japanese Kokai Publication Hei-8-119969), or 2,4,5-trialkylbenzaldehyde (Japanese Kokai Publication Hei-7-2864, U.S. Pat. No. 5,387,699) as a starting material.

However, none of these technologies provide pyromellitic anhydride of high purity at low cost. The technology disclosed in Japanese Kokai Publication Hei-7-2864 and U.S. Pat. No. 5,387,699, for instance, is a production method of pyromellitic anhydride which comprises subjecting either a 2,4,5-trialkyl benzaldehyde or a 2,4,5-trialkyl benzaldehyde and 1,2,4,5-tetraalkyl benzene to heterogeneous catalytic oxidation in gas phase with a molecular oxygen-containing gas in the presence of a catalyst comprising the oxide or oxides of one or more transition metals of IV subgroup of the periodic table of the elements, the oxide or oxides of one or more transition metals of V subgroup of the periodic table of the elements, the oxide or oxides of one or more elements of I main-group of the periodic table of the elements and/or the oxide or oxides of one or more elements of III, IV and V main-groups and elements of IV and VII subgroups of the periodictable of the elements in a specified weight ratio. Here, the reaction yield is only as low as 90 mass % (61 mole %) at best and it is not satisfactory. Therefore, there has been room for further studies for a method of producing pyromellitic anhydride of high purity in good yield and at low cost.

SUMMARY OF THE INVENTION

In light of the above state of the art, the present invention has for its object to provide a production method of pyromellitic anhydride of high purity in good yield at low cost by catalytic gas-phase oxidation of a 2,4,5-trialkylbenzaldehyde with the aid of a suitable catalyst system.

The inventors of the present invention investigated the technologies for producing pyromellitic anhydride of high purity at low cost and found that when (1) a catalyst the catalytic active component of which has a specific surface area of not greater than 50 m$^2$/g or (2) a catalyst the essential catalytic active component of which is vanadium as well as molybdenumand/or tungsten is used in the production of pyromellitic anhydride by catalytic gas-phase oxidation of a 2,4,5-trialkylbenzaldehyde, pyromellitic anhydride can be produced in high yield at low cost, thus giving a neat solution to the above problems. They found also that pyromellitic anhydride of high purity can be produced more positively when the catalytic active component contains certain metal elements or metal oxides and have accordingly perfected the present invention.

The present invention, therefore, is concerned with a production method of a pyromellitic anhydride comprising a step for catalytic gas-phase oxidation of a 2,4,5-trialkylbenzaldehyde with a molecular oxygen-containing gas wherein said step for catalytic gas-phase oxidation is carried out in the presence of a catalyst such that a specific surface area of a catalytic active component thereof is not greater than 50 m$^2$/g.

The present invention further relates to a production method of a pyromellitic anhydride comprising a step for catalytic gas-phase oxidation of a 2,4,5-trialkylbenzaldehyde with a molecular oxygen-containing gas wherein said step for catalytic gas-phase oxidation is carried out in the presence of a catalyst containing vanadium as well as molybde num and/or tungsten as a catalytic active component.

DETAILED DESCRIPTION OF THE INVENTION

In the following, the present invention is now described in detail.

The production method of pyromellitic anhydride according to the invention comprises a step for catalytic gas-phase oxidation of a 2,4,5-trialkylbenzaldehyde with a molecular oxygen-containing gas. As the process for producing pyromellitic anhydride thus comprises a step for catalytic gas-phase oxidation using a molecular oxygen-containing gas, the step for conversion to the anhydride can be omitted and there is no substantial formation of waste liquor so that the process is advantageous not only in economic terms but also in environmental terms. Moreover, because a 2,4,5-trialkylbenzaldehyde is used as a starting material for production, the process is advantageous in terms of the cost and stable supply of the starting material.

The above-mentioned step for catalytic gas-phase oxidation is carried out in the presence of a catalyst the catalytic active component of which has a specific surface area of not greater than 50 m$^2$/g (hereinafter referred to sometimes as catalyst (1)) o r in the presence of a catalyst containing vanadium as well as molybdenum and/or tungsten as a catalytic active component (hereinafter referred to sometimes as catalyst (2)). It should be understood that some of the catalysts which can be used in the present invention satisfy both the above requirement of said catalyst (1) and that of said catalyst (2). These catalysts may be used each independently or two or more of them may be used together. Moreover, these catalysts may be used in a suitable combination.

The morphology of the catalyst for use in the present invention is not particularly restricted but may be a supported catalyst or a molded catalyst. The supported catalyst means a catalyst obtained by coating an inert carrier with a catalytic active component and, any of the known coating techniques such as spray coating method, dipping method, rotary granulation method, and so forth can be utilized. The molded catalyst is acatalyst obtained by molding a catalytic active component and, any of the known molding techniques such as extrusion method and compression molding method and so forth can be utilized. The catalytic active component of such a catalyst means a substance having catalytic activity in the composition of a catalyst and the substance which does not satisfy this definition can be mentioned as the carrier of a supported catalyst. A molded catalyst, except in special cases, may be regarded as a catalyst consisting solely by the active substance. As for special cases, an inert inorganic powder is added as a diluent to suppress the catalytic activity.

The catalyst (1) which can be used in the present invention is a catalyst the catalytic active component of which has a specific surface area of not greater than 50 m$^2$/g, preferably within the range of 1 to 40 m$^2$/g, more preferably within the range of 5 to 30 m$^2$/g. When the specific surface area of the catalytic active component is greater than 50 m$^2$/g, the combustion activity is increased to lower the yield of pyromellitic anhydride and it is not preferable. The specific surface area of the catalytic active component can be easily controlled by adjusting the specific surface area of the in organic oxide powder used for dispersing the catalytic active substance, for example. However, this inorganic oxide powder is not essential and a control within the preferred range can be attained even in the absence of an inorganic oxide powder by modulating the constituent elements of the catalyst or the catalytic calcinating temperature. The specific surface area is the value found by the BET (Brunaer-Emmett-Teller) method.

The catalyst (1) in the invention need only be a catalyst the catalytic active component of which has the above-defined specific surface area but preferably contains vanadium as the catalytic active component, more preferably additionally contains at least one element (hereinafter referred to sometimes as Group A element) selected from the group consisting of molybdenum, tungsten, phosphorus, boron, silver, antimony, sulfur, niobium, alkaline earth metal, and rare earth elements. Addition of the Group A element in an appropriate amount improves a yield. On the other hand, the use of the Group A element in an excessive amount may lead to a decrease in catalytic activity or an increase in combustion. Therefore, this element is preferably used within the range not over 3, more preferably, not over 2 atomic ratio of the Group A element based on vanadium.

The catalyst (2) which can be used in the invention is the oxide comprising vanadium as an essential element and at least one element selected from the group consisting of molybdenum and tungsten (hereinafter referred to sometimes as Group B element). Containing molybdenum and/or tungsten in addition to vanadium improves a yield of pyromellitic anhydride but if the amount is small, the yield-improving effect is not appreciable and if added excessively, the amount of byproducts such as trimellitic acid are increased. The preferred level of addition is within the range of 0.01 to 2, more preferably, the range of 0.01 to 1 atomic ratio of the Group B element based on vanadium.

The optional but preferred additional constituent element of the catalyst (2) of the invention is at least one element selected from phosphorus, boron, silver, antimony, sulfur, niobium, alkaline earth metal, and rare earth elements (hereinafter referred to sometimes as Group C element). Thus, it is more preferable that the catalytic active component of this catalyst (2) further contain the Group C element. Use of such Group C element in an appropriate amount improves a yield but when it is used excessively, adecrease in catalytic activity or an increase in combustion occur to depress the yield of pyromellitic anhydride. Therefore, the amount of use is preferably within the range not over 1 atomic ratio of the Group C element based on vanadium.

The catalyst (1) and catalyst (2) according to the invention may each be optionally supplemented with at least one inorganic oxide selected from titanium oxide, zirconium oxide and tin oxide. By adding any of them in an appropriate amount, it becomes possible to improve the yield of pyromellitic anhydride and the heat resistance of the catalyst. Thus, more preferably said catalytic active component additionally contains at least one inorganic oxide powder selected from the group consisting of $TiO_2$, $ZrO_2$ and $SnO_2$. The preferred level of addition of such inorganic oxide may for example be such that, based on the total sum of moles of vanadium, a Group A or Group B element, and Group C element as constitution elements of said catalyst, the surface area of the inorganic oxide powder so added will be greater than 0 and up to $1\times10^5 m^2$/mole, more preferably $1\times10^2$ to $1\times10^5 m^2$/mole, most preferably up to $1\times10^2$ to $4\times10^4 m^2$/mole.

The surface area (m$^2$/mole) of the inorganic oxide powder to be added is the value found by multiplying the weight (g) of the used oxide powder by the specific surface area (M$^2$/g) of said oxide and dividing the product by the total sum of moles of used vanadium, a Group A or Group B element, and Group C element each in terms of metal. The specific surface area mentioned just above is also found by the BET method.

The preparation method and the raw materials for such catalysts are not particularly restricted but the conventional techniques and materials can be utilized. Referring to the raw materials, the inorganic salts, such as nitrates, sulfates, hydrochlorides, phosphates, carbonates, etc., the organic acid salts, such as oxalates, citrates, tartrates, etc., the complex salts, or the oxides of the elements to be used can be employed.

By the calcinating operation for catalyst preparation, these are thought to become the corresponding oxides or complex oxides in the catalyst. As to titanium oxide, zirconium oxide and tin oxide, commercial oxide powders or oxide powders prepared from the corresponding salts can be employed and those having BET specific surface areas in the range of 5 to 100 m²/g can be used preferably.

In preparing said catalyst, the starting compounds of respective elements are blended as evenly as possible. Thus, the compounds are blended by stirring in a dispersant such as water to give a liquid, a slurry or a clay-like artifact. It is also advantageous to increase the strength of the catalyst by incorporating whiskers or other fibrous matter at the same time.

For imparting a definite shape to said catalyst, the hitherto-known techniques can be used. For example, the bake-on method which comprises spray-coating a preheated heat-resistant carrier with the slurry, the rotary granulation method and the dipping method, among other supporting methods, or the extrusion molding method, etc. can be utilized.

When said supporting method is used, a material for the carrier to be used is not particularly restricted but any of the inert carriers in general use as a catalyst carrier which are stable in a high-temperature oxidizing atmosphere, such as silicon carbide, silica, alumina, steatite, earthenware, porcelain, or the like can be employed. The preferred is made of silicon carbide, and a carrier made of high-purity silicon carbide with a purity of not less than 95% can be employed with particular advantage. The shape of the carrier is not particularly restricted but granular forms such as beads, rings, hemi-rings, cylinders, cones, saddles, etc. can be used with advantage. More preferably, carriers with an apparent outer diameter of about 3 to 15 mm on the average are used.

The reaction starting material for use in the invention, namely 2,4,5-trialkylbenzaldehyde, may have an alkyl group of any arbitrary kind. However, the larger the number of carbon atoms of the alkyl group is, the greater the amount of heat generated in the oxidation reaction is. Therefore, the number of carbon atoms of the alkyl group is preferably as few as possible. Thus, a compound having alkyl groups of 1 to 3 carbon atoms can be used with advantage. Particularly, 2,4,5-trimethylbenzaldehyde can be produced with high yield by the carbonylation of 1,2,4-trimethylbenzene (hereinafter referred to sometimes as pseudocumene), which gives rise to only a small amount of heat in oxidation reaction and is comparatively inexpensive, with carbon monoxide (CO) at atmospheric temperature in the presence of $HF-BF_3$, $HSO_3F-SbF_5$, $CF_3SO_3H$ or the like and, therefore, is particularly advantageous as a starting material for low-cost production of pyromellitic anhydride.

In the present invention, the reaction may optionally be carried out using a 2,4,5-trialkylbenzaldehyde and 1,2,4,5-tetraalkylbenzene mixture as the starting material and, in that case, the proportions of the component compounds may be arbitrary.

The reaction according to the invention is preferably carried out in a fixed-bed type reactor packed with the catalyst and passing a feed gas composed of either a 2,4,5-trialkylbenzaldehyde or a 2,4,5-trialkylbenzaldehyde and 1,2,4,5-tetraalkylbenzene mixture and a molecular oxygen-containing gas through the catalyst bed in the tubular reactor held in a heat medium controlled at a predetermined temperature. For industrial production, a heat-exchange type multi-tubular reactor, which is commonly used for gas-phase oxidation reaction, comprising a plurality of tubular reactors sharing in the feed gas inlet space and outlet space and held in a heat medium can be used with advantage. The diameter of the tubular reactor is not particularly restricted but tubes having inside diameters in the range of 15 mm to 30 mm, which are used for catalytic gas-phase oxidation reactions in general, can be employed.

In the production method according to the invention, such a tubular reactor is packed with the oxide catalyst the catalytic active component of which has a specific surface area of not greater than 50 m²/g (catalyst (1)) or the oxide catalyst containing vanadium as well as molybdenum and/or tungsten (catalyst (2)) and the feed gas is passed through to carry out a catalytic gas-phase oxidation reaction. When the catalyst (2) is used, it is not necessary to use a catalyst containing molybdenum and/or tungsten throughout the entire catalyst bed but a high yield can be obtained by dividing the catalyst bed in two and using acatalyst containing molybdenum and/or tungsten only at the side of the feed gas outlet. Moreover, a similar effect can be obtained by using the reactor packed with catalysts of increasing molybdenum and/or tungsten contents from the feed gas inlet toward the gas outlet up to the point of substantial completion of the pyromellitic anhydride-producing reaction where the catalyst bed is divided into a larger number of zones.

In the present invention, the reaction conditions are not particularly restricted but the space velocity is preferably 500 to 10000 $h^{-1}$ particularly 1000 to 8000 $h^{-1}$. The reaction temperature is 300 to 500° C., preferably 350 to 450° C., in terms of the temperature of the heat medium. The concentration of the feed gas in mass per m³ of the molecular oxygen-containing gas (g/m³, standard condition) is 10 to 100 g/m³, preferably 10 to 50 g/m³.

The molecular oxygen-containing gas may be air, oxygen or a mixture gas composed of a reaction-indifferent inert gas, such as nitrogen or carbon dioxide, and oxygen.

In accordance with the production method of the invention, constituted as above, pyromellitic anhydride of high purity can be produced at low cost by the catalytic gas-phase oxidation of a 2,4,5-trialkylbenzaldehyde or a 2,4,5-trialkylbenzaldehyde and 1,2,4,5-tetraalkylbenzene mixture in the presence of a catalyst of the invention.

BEST MODE FOR CARRYING OUT THE INVENTION

The following examples illustrate the present invention in further detail without defining the scope of the invention.

It is to be understood that the pyromellitic anhydride yield (mole %) values given in the following examples and comparative examples are those measured by liquid chromatography and the yield is defined by the following expression. [(number of moles of pyromellitic anhydride produced)/(number of moles of starting material fed)] ×100.

Catalyst Preparation

Catalyst A

In 400 ml of deionized water was dissolved 240 g of oxalic acid, and 100 g of ammoniummetavanadate was added and uniformly dissolved therein. Then, 3.07 g of ammonium dihydrogen phosphate was added and mixed evenly. To this mixture, 214 g of anatase type titanium oxide with a specific surface area of 20 m²/g and 17 g of silicon carbide whiskers were added and the whole mixture was thoroughly stirred to give 600 ml of a homogeneous slurry of catalyst components. An external heating-type rotary furnace was charged with 200 ml of ring-formed silicon carbide carrier having an outer diameter of 7 mm, an inner diameter of 4 mm and a length of 7 mm and the carrier was preheated to 200 to 350° C. This heated carrier was spray-coated with the catalyst component slurry prepared above to support 10 g of the catalyst substance on the carrier while keeping the carrier temperature at 180 to 250° C. The coated carrier was fired in a furnace at 500° C. for 6 hours to give Catalyst A. The supported catalytic active substance powder was stripped off and recovered and the specific surface area was measured with 4-SOAP U2C, product of Yuasa-Ionics. The result was 14.5 m$^2$/g.

Catalyst B

Using titanium oxide with a specific surface area of 64 m$^2$/g in lieu of the above titanium oxide with a specific surface area of 20 m$^2$/g, Catalyst B was prepared in otherwise the same manner as Catalyst A. The supported catalytic active substance powder was stripped off and recovered and the specific surface area was measured. The result was 52 m$^2$/g.

Catalyst C

In 400 ml of deionized water was dissolved 240 g of oxalic acid, and 100 g of ammonium metavanadate and 15.1 g of ammonium paramolybdate were added and evenly admixed. Then, 3.07 g of ammonium dihydrogen phosphate and 6.53 g of silver nitrate dissolved in a small quantity of deionized water in advance were added and evenly admixed. To this mixture, 214 g of anatase type titanium oxide with a specific surface area of 20 m$^2$/g and 17 g of silicon carbide whiskers were added and the whole mixture was thoroughly stirred to give 600 ml of a homogeneous slurry of catalyst components. An external-heating type rotary furnace was charged with 200 ml of ring-formed silicon carbide carrier 7 mm in outer diameter and 7 mm long and the carrier was preheated to 200 to 350° C. Then, the carrier was spray-coated with the catalyst component slurry prepared above to support 10 g of the catalyst substance on the carrier while keeping the carrier temperature at 260 to 310° C.

Then, the coated carrier was fired in a furnace at 500° C. for 6 hours to give Catalyst C. The supported catalytic active substance powder was stripped off and recovered and the specific surface area was measured. The result was 18.4 m$^2$/g.

Catalyst D

Except that the use of 214 g of anatase type titanium oxide with a specific surface area of 20 m$^2$/g was omitted, Catalyst D was prepared in otherwise the same manner as Catalyst C. The supported catalytic active substance powder was stripped off and recovered and the specific surface area was measured. The result was 16.7 m$^2$/g.

Catalyst E

Except that the use of ammonium paramolybdate was omitted, Catalyst E was prepared in otherwise the same manner as Catalyst C. The supported catalytic active substance powder was stripped off and recovered and the specific surface area was measured. The result was 14.6 m$^2$/g.

Catalyst F

Using 19.8 g of ammonium metatungstate with a tungsten oxide content of 50 weight % in lieu of ammonium paramolybdate, Catalyst F was prepared in otherwise the same manner as Catalyst C. The supported catalytic active substance powder was stripped off and recovered and the specific surface area was measured. The result was 19.8 m$^2$/g.

EXAMPLE 1

A stainless steel tubular reactor 25 mm in inside diameter and 400 mm long was packed with Catalyst A to prepare a 200 mm-long catalyst bed and further with glass beads having an average diameter of 5 mm to prepare an approximately 100 mm-long preheating zone.

The reaction was carried out by passing a substrate mixture gas composed of 30 g/m$^3$ of 2,4,5-trimethylbenzaldehyde and the balance of air through the catalyst bed at a flow rate of 6.3 L/min.

At a reaction temperature of 370° C., pyromellitic anhydride was obtained in the highest yield and the yield of pyromellitic anhydride was 70.7 mole %.

COMPARATIVE EXAMPLE 1

Using Catalyst B in lieu of Catalyst A, the catalytic gas-phase oxidation of 2,4,5-trimethylbenzaldehyde was carried out in otherwise the same manner as in Example 1. At a reaction temperature of 370° C., pyromellitic anhydride was obtained in the highest yield and the yield of pyromellitic anhydride was 66.4 mole %.

EXAMPLE 2

Using Catalyst C in lieu of Catalyst A, the catalytic gas-phase oxidation of 2,4,5-trimethylbenzaldehyde was carried out in otherwise the same manner as in Example 1. At a reaction temperature of 390° C., pyromellitic anhydride was obtained in the highest yield and the yield of pyromellitic anhydride was 76.0 mole %.

EXAMPLE 3

Using Catalyst D in lieu of Catalyst A, the reaction was carried out in otherwise the same manner as in Example 1. At a reaction temperature of 390° C., pyromellitic anhydride was obtained in the highest yield and the yield of pyromellitic anhydride was 76.5 mole %.

COMPARATIVE EXAMPLE 2

Using durene in lieu of 2,4,5-trimethylbenzaldehyde as the reaction starting material, the reaction was carried out in otherwise the same manner as in Example 3. At a reaction temperature of 400° C., pyromellitic anhydride was obtained in the highest yield and the yield of pyromellitic anhydride was 59.6 mole %.

EXAMPLE 4

Using a mixture of 2,4,5-trimethylbenzaldehyde and durene (1:1, mole ratio) as the reaction starting material, the reaction was carried out in otherwise the same manner as in Example 2. As a result, pyromellitic anhydride was obtained in a yield of 68.1 mole %.

COMPARATIVE EXAMPLE 3

Using Catalyst B in lieu of Catalyst C, the reaction was carried out in otherwise the same manner as in Example 4. As a result, pyromellitic anhydride was obtained in a yield of 60.7 mole %.

EXAMPLE 5

Using Catalyst E in lieu of Catalyst A, the catalytic gas-phase oxidation reaction of 2,4,5-trimethylbenzaldehyde was carried out in otherwise the same manner as in Example 1. At a reaction temperature of 370° C., pyromellitic anhydride was obtained in the highest yield and the yield of pyromellitic anhydride was 71.4 mole %.

COMPARATIVE EXAMPLE 4

Using durene in lieu of 2,4,5-trimethylbenzaldehyde as the reaction starting material, the reaction was carried out in otherwise the same manner as in Example 5. At a reaction temperature of 370° C., pyromellitic anhydride was obtained in the highest yield and the yield of pyromellitic anhydride was 59.5 mole %.

EXAMPLE 6

Except that the bed length of Catalyst C was prepared to 150 mm and Catalyst E was packed to a 50 mm-long bed at the feed gas inlet side, the catalytic gas-phase oxidation reaction of 2,4,5-trimethylbenzaldehyde was carried out in otherwise the same manner as in Example 2. At a reaction temperature of 400 to 410° C., pyromellitic anhydride was obtained in the highest yield and the yield of pyromellitic anhydride was 75.3 mole %. The hot spot representing the highest bed temperature was situated in the catalyst bed comprised of Catalyst E.

EXAMPLE 7

Using Catalyst F in lieu of Catalyst A, the reaction was carried out in otherwise the same manner as in Example 1. At a reaction temperature of 400° C., the highest yield was attained and it was 75.1 mole %.

What is claimed is:

1. A production method of a pyromellitic anhydride comprising a step for catalytic gas-phase oxidation of a 2,4,5-trialkylbenzaldehyde with a molecular oxygen-containing gas
   wherein said step for catalytic gas-phase oxidation is carried out in the presence of a catalyst such that a specific surface area of a catalytically active component thereof is not greater than 50 m$^2$/g wherein the catalytically a active component contains vanadium.

2. The production method of a pyromellitic anhydride according to claim 1
   wherein said catalytically active component contains at least one element selected from the group consisting of molybdenum, tungsten, phosphorus, boron, silver, antimony, sulfur, niobium, alkaline earth metal and rare earth element.

3. The production method of a pyromellitic anhydride according to claim 1
   wherein said catalytically active component contains at least one inorganic oxide powder selected from the group consisting of TiO$_2$, ZrO$_2$ and SnO$_2$.

4. The production method of a pyromellitic anhydride according to claim 1 wherein said catalytically active component has the specific surface area of 1 to 40 m$^2$/g.

5. The production method of a pyromellitic anhydride according to claim 1 wherein said catalytically active component has the specific surface area of 5 to 30 m$^2$/g.

6. A production method of a pyromellitic anhydride comprising a step for catalytic gas-phase oxidation of a 2,4,5-trialkylbenzaldehyde with a molecular oxygen-containing gas
   wherein said step for catalytic gas-phase oxidation is carried out in the presence of a catalyst containing vanadium as well as molybdenum and/or tungsten as a catalytically active component.

7. The production method of a pyromellitic anhydride according to claim 6
   wherein said catalytically active component contains at least one element selected from the group consisting of phosphorus, boron, silver, antimony, sulfur, niobium, alkaline earth metal and rare earth element.

8. The production method of a pyromellitic anhydride according to claim 6
   wherein said catalytically active component contains at least one inorganic oxide powder selected from the group consisting of TiO$_2$, ZrO$_2$ and SnO$_2$.

* * * * *